(12) United States Patent
Guthrie

(10) Patent No.: US 9,566,232 B2
(45) Date of Patent: *Feb. 14, 2017

(54) COMPOSITIONS AND METHODS FOR ENHANCING THE EFFICACY OF CONTRACEPTIVE MICROBICIDES

(71) Applicant: Evofem, Inc., San Diego, CA (US)

(72) Inventor: Wendell Guthrie, Missoula, MT (US)

(73) Assignee: EVOFEM, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/864,673

(22) Filed: Sep. 24, 2015

(65) Prior Publication Data

US 2016/0008276 A1 Jan. 14, 2016

Related U.S. Application Data

(63) Continuation of application No. 14/410,841, filed as application No. PCT/US2013/032510 on Mar. 15, 2013.

(60) Provisional application No. 61/659,368, filed on Jun. 13, 2012.

(51) Int. Cl.

| A61K 9/06 | (2006.01) |
| A61K 31/19 | (2006.01) |
| A61K 9/00 | (2006.01) |
| A61K 47/12 | (2006.01) |
| A61K 47/36 | (2006.01) |
| A61K 31/675 | (2006.01) |

(52) U.S. Cl.
CPC .............. *A61K 9/0034* (2013.01); *A61K 9/06* (2013.01); *A61K 31/19* (2013.01); *A61K 31/675* (2013.01); *A61K 47/12* (2013.01); *A61K 47/36* (2013.01)

(58) Field of Classification Search
None
See application file for complete search history.

(56) References Cited

U.S. PATENT DOCUMENTS

| 5,617,877 | A | 4/1997 | Moench et al. |
| 6,468,526 | B2 | 10/2002 | Chrisope |
| 6,706,276 | B2 | 3/2004 | Garg et al. |
| 8,425,894 | B2 | 4/2013 | Batcheller et al. |
| 8,518,378 | B2 | 8/2013 | Tamarkin et al. |
| 8,871,244 | B2 | 10/2014 | Andersch |
| 9,060,933 | B2 | 6/2015 | Dahl |
| 2002/0177624 | A1 | 11/2002 | Hanna et al. |
| 2004/0009223 | A1* | 1/2004 | Garg ............ A61K 9/0034 424/484 |
| 2009/0142313 | A1 | 6/2009 | Talling et al. |
| 2011/0159091 | A1 | 6/2011 | Stone et al. |
| 2015/0080467 | A1 | 3/2015 | Andersch |
| 2015/0202216 | A1 | 7/2015 | Guthrie |

FOREIGN PATENT DOCUMENTS

| AU | 2015201042 A1 | 9/2015 |
| WO | WO-0138284 A1 | 5/2001 |
| WO | WO-0166084 A2 | 9/2001 |
| WO | WO-03000224 A1 | 1/2003 |
| WO | WO-2009155118 A1 | 12/2009 |
| WO | WO-2010138823 A1 | 12/2010 |
| WO | WO-2013187984 A1 | 12/2013 |
| WO | WO-2015027071 A1 | 2/2015 |

OTHER PUBLICATIONS

Malinova. Lactobor Intim vaginal gel for the treatment and prevention of bacterial vaginosis. Akush Ginekol (Sofiia) 48(Suppl) 2:32-33 (2009) (English translation).
O'Hanlon et al. In vaginal fluid, bacteria associated with bacterial vaginosis can be suppressed with lactic acid but not hydrogen peroxide. BMC Infect Dis 11:200 (2011).
PCT/US2013/32510 International Preliminary Report on Patentability dated Feb. 2, 2014.
PCT/US2013/32510 International Search Report and Written Opinion dated Jun. 5, 2013.
Purcell et al. Biology of mucosally transmitted sexual infection-translating the basic science into novel HIV intervention: a workshop summary. AIDS Res Hum Retroviruses 28(11):1389-1396 (2012).
Owen et al. A Review of the Physical and Chemical Properties of Human Semen and the Formulation of a Semen Simulant. J Androl 26(4):459-469 (2005).
U.S. Appl. No. 14/410,841 Office Action dated May 19, 2016.

\* cited by examiner

*Primary Examiner* — Jessica Worsham
(74) *Attorney, Agent, or Firm* — Wilson, Sonsini, Goodrich & Rosati

(57) ABSTRACT

The present disclosure relates to compositions and methods for contraception that also enhance the efficacy of microbicides. Such compositions serve the dual purpose of preventing pregnancy and lessening the risk of spreading sexually transmitted diseases. More specifically, the compositions and methods relate to syngergistic contraceptive microbicide and antiviral compositions comprising a combination of a contraceptive microbicide and an antiviral agent in an acidic carrier that enhances the efficacy of both the contraceptive microbicide and antiviral agent.

16 Claims, No Drawings

COMPOSITIONS AND METHODS FOR ENHANCING THE EFFICACY OF CONTRACEPTIVE MICROBICIDES

CROSS REFERENCE

This application is a continuation application of U.S. application Ser. No. 14/410,841, filed Dec. 23, 2014, which is a U.S. National Phase of PCT/US2013/032510, filed Mar. 15, 2013, which claims the benefit of priority to U.S. Provisional Application No. 61/659,368, filed Jun. 13, 2012, each of which is herein incorporated by reference in its entirety.

TECHNICAL FIELD

The present disclosure relates to compositions and methods for contraception that also enhance the efficacy of microbicides. Such compositions serve the dual purpose of preventing pregnancy and lessening the risk of spreading sexually transmitted diseases.

BACKGROUND OF THE INVENTION

Human immunodeficiency virus (HIV), the etiologic agent of acquired immunodeficiency syndrome (AIDS) is the fastest growing cause of death in women of reproductive age. Worldwide, the heterosexual transmission of AIDS is the prevalent mode of transmission of AIDS, accounting for about 90% of all HIV infections in women. Therefore, significant attention has been directed to investigating measures that block sexual spreading of HIV infection. As there is no effective treatment or vaccine against AIDS, preventive measures are the primary tools that can presently reduce transmission of HIV. For example, the consistent and correct use of condoms represents an effective barrier to prevent HIV transmission. However, the risk of acquiring infection can only be significantly reduced if condoms are used for almost all sexual intercourse in HIV prevalent communities; a result that can not be achieved despite intensive prevention programs to increase condom use.

Significant emphasis has been placed on the development of intravaginal microbicidal agents capable of preventing and/or reducing the spread of a variety of sexually transmitted diseases (STDs) in addition to Herpes Simplex Virus (HSV) and HIV. The development of microbicides for topical use represents an important alternative to condom usage. A microbicide is any agent that kills or deactivates disease-causing microbes, including viruses. According to the International Association of Physicians in AIDS CARE (IAPAC), the definition of microbicides also includes interventions that can block or prevent infection, as well as amplification of the body's natural defenses to prevent infection through sexual acts.

Ideally, microbicides should have little or no side effects at an effective microbicidal concentration. Accordingly, the drug used as a microbicide should have little or no immunosuppressive activity at an effective microbicidal concentration. In addition, the ideal microbicide should sufficiently withstand varying temperatures and acceptably function within varied pH ranges (ranges of alkaline and acidic levels in the vagina). Further, it should not eliminate the natural beneficial lactobacilli that reside in the vagina and contribute to vaginal health.

Topical microbicides would be even more beneficial if they also had contraceptive capabilities. Contraception is also important for women with STDs to prevent transmitting diseases future generation, especially since many women with STDs are of childbearing age. At present, a majority of commercially available dual-purpose spermicidal microbicides have detergent ingredients that disrupt cell membranes. The most widely used vaginal spermicide, nonoxynol-9 (N-9), because of its membrane disruptive properties, has been shown to damage the cervicovaginal epithelium, cause an acute inflammatory tissue response, alter vaginal microflora, and enhance the risk of promoting opportunistic infections in the genitourinary tract. N-9 is also toxic to vaginal and cervical cells which increases the permeability of vaginal tissue. It can also kill the *Lactobacillus* sp. that populate the vaginal tract and are generally regarded as beneficial. *Lactobacillus* produce lactic acid and hydrogen peroxide, which helps maintain the acidic pH of the vagina (~pH 3.5 to 5.0) and a healthy vaginal flora. At this pH, a number of STD-causing organisms like HIV are inactivated.

Other spermicidal microbicides in the form of vaginal creams and ointments are currently available over the counter or by prescription. Still others are in various stages of development. Examples include octoxynol-9 and benzalkonium chloride. Gels designed to control vaginal pH are also available, such as AciJel™ (Ortho-McNeil Pharmaceutical Corp., Raritan, N.J.) which is a water dispersible buffered gel having a pH of 3.9 to 4.1. It is used to restore and maintain normal vaginal acidity. Such gels are designed to control vaginal pH and are not specifically designed to prevent STDs and/or contraception, and thus do not always possess effective microbicidal activity.

As discussed, presently marketed vaginal contraceptive compositions, often containing N-9 as an active ingredient, are generally known in the art. While presently marketed vaginal contraceptive formulations aid in preventing pregnancy, their ability to effectively prevent STDs, particularly HIV/AIDS, is very limited. Moreover, recent analyses show that N-9, when used frequently by women at high risk may actually increase the risk of HIV infection (WHO 2002, WHO/CONRAD technical consultation on nonoxynol-9, Geneva).

Additionally, several microbicides under development contain anti-retroviral agents that had originally been developed for the treatment of patients with HIV infection. However, only temporary and limited benefits are observed in HIV-infected patients treated with any of the actual anti-retrovirals or combinations thereof. The limited ability of these agents to decrease viral burden, the rapid development of resistance and the toxic side-effects of most drugs has limited their long-term efficacy. One major problem associated with the administration of antiviral agents to patients is their poor ability to penetrate and target infected cells. Rapid drug clearance and the toxicity of parent compounds or metabolites also constitute some of the major drawbacks that may slow down the development and use of many antiviral agents. Given the severe toxicity of antiviral agents actually available to treat AIDS and other viral diseases and their limited ability to target infected cells, strategies aimed at reaching therapeutic levels of drugs into infected cells and reducing toxicity is needed.

One of the more recently studied antimicrobials is BufferGel™ (ReProtect LLC, Baltimore, Md.), which has undergone clinical trials. It is a negatively charged, non-absorbable, high molecular weight polymer gel that is designed to maintain vaginal pH below 5 in the presence of semen. As detailed in U.S. Pat. No. 5,617,877, BufferGel™ formulated from a polymer comprised of carboxylated monomers. The polymers have buffering capacity which help control the vaginal pH. However, for contraceptive purposes, Buffer- Gel™ is designed to be used with a device to be inserted into the vagina and positioned over the cervix. As such, to be effective, the device must remain in position over the cervix. Removal of the device or a shift of its position relative to the cervix can destroy, or at least significantly reduce, its effectiveness.

Recent studies have shown that a significant contribution to the antimicrobial properties naturally present in the vagina is primarily due to the microbicidal activity of the lactic acid molecule, and is not necessarily due to low pH alone or to the presence of hydrogen peroxide. (O'Hanlon et al., BMC Infect Dis., 11:200, 2011). In particular, it has been shown that in vaginal fluid, bacteria associated with bacterial vaginosis can be suppressed with lactic acid, but to a much lesser extent with other acids at the same pH.

Accordingly, there is a need for dual purpose contraceptive microbicide and antiviral compositions and methods that provide improved contraceptive and microbicidal activity in order to prevent or reduce the risk of transmission of STDs, including HIV and HSV-2 while simultaneously preventing unwanted pregnancies. Such compositions should be useful for vaginal administration in effective doses that do not inactivate *Lactobacillus* sp. or cause overt vaginal irritation or other toxicity.

SUMMARY OF THE INVENTION

The embodiments disclosed below satisfy this need. The following simplified summary is provided in order to establish a basic understanding of some aspects of the claimed subject matter. This summary is not an extensive overview, and is not intended to identify key/critical elements or to delineate the scope of the claimed subject matter.

In an exemplary embodiment, the present disclosure is directed to contraceptive microbicide and antiviral compositions and methods of use thereof, such compositions including: (a) an effective amount of a bioadhesive (wherein the bioadhesive includes (i) a matrix-forming compound; (ii) a bioadhesive compound that may be the same or different from the matrix-forming compound; and (iii) lactic acid); (b) 1-(6-aminopurin-9-yl)propan-2-yloxymethylphosphonic acid, or a physiologically functional derivative thereof; and (c) a pharmaceutically acceptable carrier. In various embodiments, such compositions generally have a pH of 5.0 or below, and in further embodiments, such compositions are not in a matrix state until they come in contact with ejaculate. In other embodiments, the lactic acid is L-lactic acid.

In additional embodiments of the present disclosure, the compositions may also include a humectant and/or a preservative.

In another embodiment, the present disclosure is directed to contraceptive microbicide and antiviral compositions and methods of use thereof, such compositions including: (a) a matrix-forming compound; (b) a bioadhesive compound that may be the same or different from the matrix-forming compound; (c) lactic acid; (d) 1-(6-aminopurin-9-yl)propan-2-yloxymethylphosphonic acid or a physiologically functional derivative thereof; and (e) a pharmaceutically acceptable carrier. In various embodiments, such compositions generally have a pH of 5.0 or below, and in further embodiments, the compositions have buffering capabilities such that the pH is maintained below 5.0 in the presence of a normal amount of ejaculate.

Other aspects of the disclosure are found throughout the specification.

DETAILED DESCRIPTION OF THE INVENTION

Disclosed herein are compositions and methods for contraception that also enhance the efficacy of microbicides. Such compositions serve the dual purpose of preventing pregnancy and lessening the risk of spreading sexually transmitted diseases. More specifically, the compositions and methods disclosed herein relate to synergistic contraceptive microbicide and antiviral compositions comprising a combination of a contraceptive microbicide and an antiviral agent in an acidic carrier that enhances the efficacy of both the contraceptive microbicide and antiviral agent.

To facilitate understanding of the disclosure that follows, a number of terms are defined below.

When the terms "one," "a," or "an" are used in this disclosure, they mean "at least one" or "one or more," unless otherwise indicated.

As used herein, the terms "microbicide" and "microbicidal" refer to a compound capable of preventing or inhibiting the growth and/or preventing or reducing the infectivity of microbes, including viruses, bacteria, fungi and algae.

As used herein, the term "sexually transmitted disease" is used interchangeably with "STD," "sexually transmitted infection," "STI" and/or the plural thereof. An STD is an illness or pathophysiological condition that has a significant probability of transmission between humans by means of any form of sexual contact, including kissing. The term STD may also encompass a person who is infected, and may potentially infect others, without showing signs of disease or infection.

The terms "synergy" and "synergistic" mean that the effect achieved with the compounds used together is greater than the sum of the effects that results from using the compounds separately, i.e. greater than what would be predicted based on the two active ingredients administered separately. A synergistic effect may be attained when the compounds are: (1) co-formulated and administered or delivered simultaneously in a combined formulation; (2) delivered by alternation or in parallel as separate formulations; or (3) by some other regimen. A synergistic antiviral effect denotes an antiviral effect which is greater than the predicted purely additive effects of the individual compounds of the combination.

As used herein, the term "physiologically functional derivative" refers to a pharmaceutically active compound with equivalent or near equivalent physiological functionality to Acidform or tenofovir when administered in combination with another pharmaceutically active compound in a combination of the disclosure. As used herein, the term "physiologically functional derivative" includes any: physiologically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antiviral-active metabolite or residue thereof.

As used herein, the term "contacting" refers to any suitable method of bringing one or more of the contraceptive microbicide and antiviral compounds described herein into contact with a sexually-transmitted or sexually-acquired microbe or microbial cell, as described herein. In vitro or ex vivo, this is achieved by exposing the microbe or microbial cell to the microbicide in a suitable medium. For exemplary in vivo applications, topical methods of administration are suitable as described herein.

As used herein, the term "matrix" is meant to refer to a plurality of different molecules that form a three-dimensional structure via ionic interactions there between.

The term "pH of 4 or below" means a pH that is less than 4.5.

The term "buffering capabilities" means the ability to maintain a desired pH when contacted with a compound having a different pH. In particular, buffering capabilities means the ability to maintain a healthy vaginal pH in the presence of normal amounts of ejaculate.

The term "contacted with ejaculate" means the presence of semen in the volume normally occurring during ejaculation, e.g., between 0.1 to 11 milliliters (Rehan, et al., Fertil Steril. 1975, 26:492-502).

The contraceptive microbicide and antiviral compositions and methods disclosed prevent or reduce the risk of the transmission of STDs and/or common vaginal infections. STDs include, but are not limited to, HIV/AIDS, herpes (caused by herpes simplex virus type 1 (HSV-1) or herpes simplex virus type 2 (HSV-2), gonorrhea, chlamydia, syphilis, and trichomoniasis. Non-limiting examples of common vaginal infections include bacterial vaginosis (BV) and vaginal candidiasis. Similar compositions and methods of application of such compositions, as described herein, can be used for preventing or treating STDs and/or common vaginal infections.

The compositions of the present disclosure comprise a combination of a bioadhesive agent with contraceptive and microbicidal properties (i.e. a "contraceptive microbcide") and a particular antiviral agent, tenofovir. The contraceptive microbicide has bioadhesive properties and buffering capabilities. Upon contact with semen, the contraceptive microbicide forms a matrix that traps the sperm, and the buffering capabilities keep the pH at a low level further inactivating the sperm. Tenofovir is an antiretroviral drug designed to inhibit reverse transcriptase. The prodrug form of tenofovir, tenofovir disproxyl fumarate, has been approved by the U.S. Food and Drug Administration for treating HIV and chronic hepatitis B and may be effective against other viruses such as herpes. (Andrei, et al., Cell Host Microbe., 10:379-89, 2011). In exemplary embodiments, a synergistic effect is achieved between the two components. More particularly, the negatively charged monophosphate moiety of tenofovir forms ionic interactions with the matrix forming agent and/or bioadhesive compound, which is further enhanced by lactic acid. When the matrix is formed, it facilitates prolonged release of the tenofovir, thus enhancing efficacy.

It is further believed that the compositions of the present disclosure exhibit improved efficacy because the tenofovir concentration is maintained between effective and toxic levels, due to the fact that the matrix formation and bioadhesive properties inhibit the dilution of the drug away from the delivery point, thereby improving targeting and localization of the drug. In this context, bioadhesion increases the intimacy and duration of contact between the tenofovir and the mucosal surface. The combined effects of this enhanced, direct drug absorption, and the decrease in excretion rate that results from reduced diffusion and improved localization significantly enhances bioavailability of the drug and allows for a smaller dosage and less frequent administration.
Tenofovir (Gilead Science, Inc.)

Tenofovir, which includes derivatives, analogues, prodrugs and salts thereof, belongs to a class of antiretroviral drugs known as nucleotide analogue reverse transcriptase inhibitors (NtRTIs), which block reverse transcriptase. It has the chemical name 1-(6-aminopurin-9-yl)propan-2-yloxymethylphosphonic acid [CAS Registry number: 147127-20 ¬6]. The structure of tenofovir is shown below:

Tenofovir is a competitive inhibitor of other naturally occurring nucleotides, and its ultimate biological activity is viral DNA chain termination. Tenofovir is a novel nucleotide analog with antiviral activity against both HIV and Hepatitis B. The mechanism of tenofovir is similar to that of

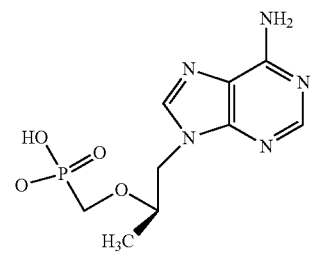 [SMILES: C[C@H](Cn1cnc2c(N)ncnc21)OCP(=O)(O)O]

nucleoside analogs, which interferes with reverse transcriptase and prevents translation of viral genetic material into viral DNA. Unlike the nucleoside analogs, the NtRTIs are chemically pre-activated with the presence of a phosphate group. Since the phosphorylation step is not necessary, nucleotide analogs can incorporate into viral DNA chain more rapidly than nucleoside analogs. More importantly, this will bypass a viral mechanism of nucleoside resistance.
Contraceptive Microbicide In one embodiment, the contractive microbicide is Acidform (also known as Amphora® (U.S. Pat. No. 6,706,276, WO 01/66084), which is a gel that, when placed in a body orifice (e.g., vagina), forms a matrix upon contact with ejaculate and thus entraps and inactivates spermatozoa and/or STD and STI-causing microbes. In one general embodiment, the contraceptive microbicide contains (1) a matrix-forming compound, (2) a bioadhesive compound, and (3) lactic acid. Some compounds, such as chitosan, can act as both the matrix-forming compound and the bioadhesive compound.

In exemplary embodiments, the Acidform used generally contains (1) about 1-10% of one or more matrix-forming compounds, (2) about 1-10% of one or more bioadhesive compounds, and (3) about 1-10% of lactic acid. In other embodiments of, the Acidform composition contains (1) about 3-5% of one or more matrix-forming compounds, (2) about 2.5-6% of one or more bioadhesive compounds, and (3) about 1-7% of lactic acid. In other embodiments, the Acidform composition contains (1) about 3.5-4.5% of one or more matrix-forming compounds, (2) about 2.5-3.5% of one or more bioadhesive compounds, and (3) about 1-4% of lactic acid.

In other exemplary embodiment, the Acidform used generally contains (1) about 1-10% of one or more matrix-forming compounds, (2) about 1-10% of one or more bioadhesive compounds, and (3) about 1-10% of L-lactic acid. In other embodiments, the Acidform composition contains (1) about 3-5% of one or more matrix-forming compounds, (2) about 2.5-6% of one or more bioadhesive compounds, and (3) about 1-7% of L-lactic acid. In other embodiments, the Acidform composition contains (1) about 3.5-4.5% of one or more matrix-forming compounds, (2) about 2.5-3.5% of one or more bioadhesive compounds, and (3) about 1-4% of L-lactic acid.

Matrix-forming compounds suitable for use in the present disclosure should be stable over a wide pH range, especially over the normal acidic pH values found in the vagina. Suitable matrix-forming compounds include, for example, alginic acid, chitosan, gellan gum, poloxamer, and the like. Alginic acid is a generally linear glycouronan polymer containing a mixture of -(1,4)-D-gulosyuronic acid and -(1,4)-D-gulosyuronic acid residues. Generally, the molecular weight of the alginic acid is the range of about 20,000 to about 300,000 g/mole, in other embodiments in the range of about 20,000 to about 250,000 g/mole, and in further embodiments about 240,000 g/mole. Alginic acid is expected to form insoluble alginates by interacting with monovalent and divalent cations (especially $Na^+$, $K^+$, and $Ca^{++}$) in seminal plasma. Since vaginal fluids generally contain very little $Ca^{++}$, the semisolid matrix is formed only when ejaculate is present. In such cases, the semisolid matrix will trap STD-causing microbes and spermatozoa so that they cannot migrate through the lower female genital tract. Alginates also swell in contact with water, thereby assisting in maintaining the desired gel or matrix structure within the vagina. Of course, alginic acid or salts of alginic acid may also contribute to the acid buffering activity of Acidform since they have a pH of about 1.5 to about 3.5 in an aqueous solution. Furthermore, alginic acid may also contribute to the bioadhesive nature of the present formulations and, therefore, assist in providing bioadhesive activity. Because of its high molecular weight, alginic acid will not be absorbed by the body. Thus, its matrix-forming, bioadhesive, and acid-buffering properties will be maintained so as long as the gel remains in the vagina. Moreover, due to the innate bioadhesive properties of the trapping gel, it will normally remain within the vagina for about 12 to 24 hours (or even longer) if not removed by the woman.

Bioadhesive compounds suitable for use in the present disclosure include, for example, xanthan gum, hydroxypropyl cellulose, hydroxypropyl methyl cellulose, sodium carboxymethyl cellulose, chitosan, polycarbophil, carbopol, and the like. In at least one embodiment, the bioadhesive compound is xanthan gum, a high molecular weight polysaccharide gum containing D-glucosyl, D-mannosyl, and D-glucosyluronic acid residues and varying proportions of 0-acetyl and pyruvic acid acetal. The primary structure is a cellulose backbone with trisaccharide side chains; the repealing unit is a pentasaccharide. Generally, the molecular weight is greater than about 106 g/mole.

The contraceptive microbicide further comprises lactic acid or other buffering agents that act maintain the pH of the vagina within its normal acidic range (i.e., a pH of less than about 5 and more preferably in the range of about 3.5 to about 4.5) even in the presence of normal amounts of ejaculate. Besides lactic acid, suitable buffering agents include, but are not limited to, for example, citric acid, potassium acid tartrate, benzoic acid, alginic acid, sorbic acid, fumaric acid, ascorbic acid, stearic acid, oleic acid, tartaric acid, edetic acid ethylenediaminetetracetic acid, acetic acid, malic acid, and the like. The acids may be added as free acids, hydrates, or pharmaceutically acceptable salts. Of course, the free acids can be converted to the corresponding salts in situ (i.e., within the vagina). In various exemplary embodiments, several buffering agents are included in the Acidform composition to provide increased buffering capacity. Alginic acid, of course, can function as both a matrix-forming agent and a buffering agent. Since alginic acid will not be absorbed by the body, its acid buffering effect will be longer lasting as compared to the other buffering agents which may be absorbed by the body.

Pharmaceutically Acceptable Carrier

In one embodiment, the pharmaceutical carrier is water. Other pharmaceutically acceptable carriers that are suitable for vaginal delivery are well know and can be used in place of water. One example of a suitable pharmaceutically acceptable carrier is petrolatum, such as white petrolatum.

Optional Ingredients

Additional optional excipients that may be used in the compositions of the present disclosure may also include humectants. Suitable humectants include, but are not limited to, for example, glycerol, polyethylene glycols, propylene glycols, sorbitol, triacetin, and the like. In one exemplary embodiment, glycerol is used to prevent the formation of a dry film on the gel when placed within the vagina. Glycerol may also act as a lubricant. Additionally, the compositions may also include a preservative. Suitable preservatives include, but are not limited to, for example, benzoic acid, sodium benzoate, methylparaben, ethylparaben, butylparaben, propylparaben, benzyalkonium chloride, phenylmercuric nitrate, chlorhexidine, and the like. In one exemplary embodiment, benzoic acid is used and may also contribute to the buffering capacity of the Acidform gel.

In one exemplary embodiment of the present disclosure, the contraceptive microbicide is further described as follows: the matrix-forming compound is alginic acid; the bioadhesive compound is xanthan gum and/or hydroxycellulose; lactic acid is used or is substituted by citric acid, benzoic acid or potassium acid tartrate; glycerol is included as a humectant; benzoic acid is used as a preservative; and water is the pharmaceutically acceptable carrier. In another embodiment, the composition contains xanthan gum, alginic acid, lactic acid, citric acid, benzoic acid, potassium bitartrate, glycerol, and water. In another embodiment, the lactic acid is L-lactic acid.

As discussed, lactic acid or other suitable buffering agents are used to maintain the pH of the vagina within its normal acidic range (i.e., a pH of less than about 5 and more preferably in the range of about 3.5 to about 4.5) even in the presence of normal amounts of ejaculate. In particular, it has been discovered that lactic acid significantly increases the microbicidal potency in relation to other natural vaginal defense mechanisms, such as hydrogen peroxide. This feature was previously unknown to those of skill in the art, and the inventors of the present disclosure have surprisingly found that the contraceptive microbicide, when formulated using lactic acid as a buffering agent, possesses significantly greater microbicidal activity than formulations that do not use lactic acid as a buffering agent.

Specifically, the presence of lactic acid results in greater inactivation of microbes, including viruses, in comparison to compounds such as hydrogen peroxide or acetic acid at equivalent pH. The mechanism of action by which lactic acid increases microbicidal potency is believed to be the disruption of the cell membranes of gram-negative bacteria, and also acts to inactivate HIV and HSV-2.

More specifically, lactic acid has two isomers, one is known as L-(+)-lactic acid or (S)-lactic acid and the other is D-(−)-lactic acid or (R)-lactic acid. Recent discovery has shown that the L form of lactic acid is more potent in inactivating HIV than D or racemic lactic acid. While the precise mechanism of how L-lactic acid invactivates HIV is unknown, the stereochemical dependent activity suggests that it acts on proteins. (Purcell et al., AIDS Res Hum Retroviruses. 2012 November; 28(11):1389-96.)

Lactic acid is produced by lactic acid bacteria such as *Lactobacillus* species. However, lactic acid bacteria generally produce both D and L lactic acid. Furthermore, lactic acid bacteria can be difficult to grow. Recombinant methods can be used to specifically manufacture L-lactic acid using hosts that easier to grow such as yeast or *Escherichia coli*. (Ishida et al., Appl Environ Microbiol. 2005 April; 71(4): 1964-1970 and Dien et al., 7 Ind Microbiol Biotechnol. 2001 October; 27(4):259-64.) Alternatively, purified L-lactic acid can be purchased from established chemical suppliers such as Sigma-Aldrich® (St. Louis, Mo.).

The pharmaceutical composition may be in the form of a gel, a semi-solid, a cream, and/or a lotion. Generally, the microbicide may be administered as a topical ointment applied to the lining of the vagina and/or cervix and/or rectum, which can be accomplished as a gel, cream, lotion, non-aqueous or aqueous solution used to flush the vaginal or rectal cavity, and/or a vaginal or rectal suppository. In other embodiments, the contraceptive microbicide and antiviral composition may be administered in a spray formulation. In addition, the contraceptive microbicide and antiviral compositions may be delivered using microbicide-impregnated diaphragms and female and male condoms.

Furthermore, in addition to the contraceptive microbicide and antiviral compositions disclosed herein, the balance of the compositions, i.e., typically from about 0-10% weight, or from about 0.1-5% weight, or from about 0.1-3% weight, may optionally comprise one or more cosmetic ingredients. Such cosmetic ingredients are known to those skilled in the art and are often referred to in the art as diluents, solvents, and adjuvants. Typically, cosmetic ingredients include, for example; water, ethyl alcohol, isopropyl alcohol, glycerin, glycerol propylene glycol, sorbitol, and other high molecular weight alcohols. In addition, contraceptive compositions may contain minor amounts of other additives, such as, for example; stabilizers, surfactants, menthol, eucalyptus oil, other essential oils, fragrances, and the like. The selection and amounts of cosmetic ingredients, other additives, and blending procedures can be carried out in accordance with techniques well-known in the art.

In exemplary embodiments, the present disclosure involves the topical application of contraceptive microbicide and antiviral compositions as described herein. In the context of the present disclosure, it is to be understood that the term topical application includes application the body cavities as well as to the skin. Thus, for example, the aforementioned compositions are applied to a body cavity such as the vagina, anus, rectum or mouth. Furthermore, the topical application may be carried out before, during or after intercourse, or alternatively, carried out independent from intercourse.

It is to be understood that the contraceptive microbicide and antiviral compositions of the present disclosure may be delivered to the vagina of a mammal by any means known to those skilled in the art. Typical forms for delivery of the compositions include, for example; creams, lotions, gels, foams, intervaginal devices such as sponges and suppositories, and films. In addition, the contraceptive microbicide and antiviral compositions may be used as personal care products, such as, for example, condom lubricants, and the like. Such lubricants may comprise commonly known ingredients such as, for example: humectants, e.g., glycerin, sorbitol, mannitol, glycols and glycol ethers; buffers, e.g., glucono-d-lactone; germicides or bactericides, e.g., chlorhexidine gluconate; preservatives, e.g., methylparaben; viscosifiers, e.g., hydroxyethyl cellulose, etc.; other adjuvants, e.g., colors and fragrances; in addition to the compositions of the present disclosure. Those skilled in the art will recognize that the physical properties, e.g., viscosity, of such delivery forms may vary widely. For example, the viscosity of a gel form of the composition of the present disclosure, e.g., 150,000 centipoise, may be substantially higher than the viscosity of lotion form of the composition of the present disclosure, e.g., 100 centipoise. Further details concerning the materials, ingredients, pro-portions and procedures of such delivery forms can be selected in accordance with techniques well-known in the art.

In various embodiments, the contraceptive microbicide and antiviral compositions of the present disclosure are preferably administered to the vagina of the mammal in a dosage which is effective to immobilize sperm present in the vagina and/or to inhibit their penetration in cervical mucus. Typical dosages range between about 1-10 grams, or between 3-7 grams, or between 4-6 grams of the composition.

It will be readily apparent to those skilled in the art that other compounds functioning as precursors, analogs and derivatives such as salts and esters of the present compounds can be utilized.

The disclosure set forth above is provided to give those of ordinary skill in the art a complete disclosure and description of how to make and use embodiments of the compositions and methods, and are not intended to limit the scope of what the inventors regard as their invention. Modifications of the above-described modes (for carrying out the disclosure that are obvious to persons of skill in the art) are intended to be within the scope of the following claims. All publications, patents, and patent applications cited in this specification are incorporated herein by reference in their entirety as if each such publication, patent or patent application were specifically and individually indicated to be incorporated herein by reference.

What is claimed is:

1. A method of reducing the risk of transmitting sexually transmitted infections (STIs) or vaginal infections comprising intravaginally administering a composition to a subject in need thereof, wherein the composition comprises:
    (a) a matrix-forming compound selected from the group consisting of: alginic acid, chitosan, gellan gum, and poloxamer;
    (b) a bioadhesive compound that is the same or different from the matrix-forming compound;
    (c) L-lactic acid; and
    (d) an aqueous-based pharmaceutically acceptable carrier, wherein the composition has a nonmatrix state when not in contact with ejaculate, and a matrix state when in contact with ejaculate, and wherein the composition is essentially free of D-lactic acid.

2. The method of claim 1, wherein the composition further comprises a humectant.

3. The method of claim 2, wherein the humectant is selected from the group consisting of: glycerol, polyethylene glycol, propylene glycol, sorbitol, and tiracetin.

4. The method of claim 1, wherein the composition further comprises a preservative.

5. The method of claim 4, wherein the preservative is selected from the group consisting of: benzoic acid, sodium benzoate, methylparaben, ethylparaben, butylparaben, propylparaben, benzyalkonium chloride, phenylmercuric nitrate, and chlorhexidine.

6. The method of claim 1, wherein the matrix-forming compound is alginic acid.

7. The method of claim 1, wherein the bioadhesive compound is selected from the group consisting of: xanthan gum, alginic acid, hydroxypropyl cellulose, hydroxypropyl methyl cellulose, sodium carboxymethyl cellulose, chitosan, polycarbophil, and carbopol.

8. The method of claim 7, wherein the bioadhesive compound is xanthan gum.

9. The method of claim 1, wherein the matrix resulting from contact with ejaculation traps spermatozoa.

10. The method of claim 1, wherein the matrix resulting from contact with ejaculation traps sexually transmitted disease-causing microbes.

11. The method of claim 1, wherein the composition contains about 1-10% of the matrix forming compound, 1-10% the bioadhesive compound, and/or 1-10% L-lactic acid.

12. The method of claim 1, wherein the composition contains about 3-5% of the matrix forming compound, 2.5-6% of the bioadhesive compound, and/or 1-7% L-lactic acid.

13. The method of claim 1, wherein the composition contains about 3.5-4.5% of the matrix forming compound, 2.5-3.5% of the bioadhesive, and/or 1-4% of L-lactic acid.

14. A method of reducing the risk of transmitting sexually transmitted infections (STIs) or vaginal infections comprising intravaginally administering a composition to a subject in need thereof, wherein the composition comprises:

(a) alginic acid;
(b) xanthan gum;
(c) L-lactic acid;
(d) glycerol;
(e) benzoic acid;
(f) citric acid;
(g) potassium bitartrate; and
(h) water, wherein the composition has a nonmatrix state when not in contact with ejaculate, and a matrix state when in contact with ejaculate, and wherein the composition is essentially free of D-lactic acid.

15. The method of claim 1, wherein the STIs are selected from the group consisting of HIV infection, herpes simplex, gonorrhea, chlamydia, syphilis, trichomoniasis, and combinations thereof.

16. The method of claim 1, wherein the vaginal infections are selected from the group consisting of bacterial vaginosis, vaginal candidiasis, and combinations thereof.

* * * * *